(12) United States Patent
Eicher et al.

(10) Patent No.: US 8,674,147 B2
(45) Date of Patent: Mar. 18, 2014

(54) PROCESS FOR DEHYDROCHLORINATION OF HYDROCHLOROFLUOROALKANES

(75) Inventors: Johannes Eicher, Sehnde (DE); Ercan Uenveren, Hannover (DE); Erhard Kemnitz, Berlin (DE)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 13/638,306

(22) PCT Filed: Mar. 31, 2011

(86) PCT No.: PCT/EP2011/054980
§ 371 (c)(1),
(2), (4) Date: Sep. 28, 2012

(87) PCT Pub. No.: WO2011/121058
PCT Pub. Date: Oct. 6, 2011

(65) Prior Publication Data
US 2013/0018211 A1    Jan. 17, 2013

Related U.S. Application Data

(60) Provisional application No. 61/320,425, filed on Apr. 2, 2010.

(51) Int. Cl.
*C07C 17/23* (2006.01)
(52) U.S. Cl.
USPC ........................................................ 570/176
(58) Field of Classification Search
None
See application file for complete search history.

(56) References Cited

U.S. PATENT DOCUMENTS

| 2,673,139 A | 3/1954 | Woolf et al. |
| 2,803,679 A | 8/1957 | Conrad |
| 2,924,626 A | 2/1960 | Boyer et al. |
| 2006/0052649 A1 | 3/2006 | Kemnitz et al. |

FOREIGN PATENT DOCUMENTS

| EP | 1666411 A1 | 6/2006 |
| WO | WO 2004060806 A1 | 7/2004 |
| WO | WO 2008043720 A2 | 4/2008 |
| WO | WO 2009010472 A1 | 1/2009 |
| WO | WO 2010055146 A2 | 5/2010 |
| WO | WO 2010060868 A1 | 6/2010 |
| WO | WO 2011121057 A1 | 10/2011 |

OTHER PUBLICATIONS

Teinz, K. et al. "Highly selective metal fluoride catalysts for the dehydrohalogenation of 3-chloro-1,1,1,3-tetrafluorobutane" J. Cat. 2011, 282, 175-182.*
U.S. Appl. No. 13/637,989, filed Sep. 28, 2012, Johannes Eicher, et al.
Kemnitz, Erhard, et al—"Amorphous metal fluorides with extraordinary high surface areas", 2003, Angewandte Chemie, vol. 115, Issue No. 35, pp. 4383-4386, 6 pgs.
Rudiger, S., et al—"The fluorolytic sol-gel route to metal fluorides—a versatile process opening a variety of application fields", 2008, Perspective, The Royal Society of Chemistry, Dalton Trans. vol. 7; Issue No. 9; pp. 1117-1127; 11 pgs.

* cited by examiner

*Primary Examiner* — Johann R Richter
*Assistant Examiner* — Medhanit Bahta

(57) ABSTRACT

A process for the selective dehydrochlorination of a hydrochlorofluoroalkane by using chloride fluorides of Ba, Ca, or Sr as catalysts, wherein the hydrochlorofluoroalkane comprises a carbon atom or carbon atoms carrying at least one chlorine and at least one fluorine atom and further comprises at least one hydrogen atom on a carbon atom vicinal to the carbon atom or to the carbon atoms carrying the at least one chlorine and at least one fluorine atom.

20 Claims, No Drawings

PROCESS FOR DEHYDROCHLORINATION OF HYDROCHLOROFLUOROALKANES

This application is a U.S. national stage entry under 35 U.S.C. 371 of International Application No. PCT/EP2011/054980 filed Mar. 31, 2011, which claims priority to U.S. provisional patent application No. 61/320,425 filed Apr. 2, 2010, the whole content of this application being incorporated herein by reference for all purposes.

The present invention relates to a process for dehydrochlorinating hydrochlorofluoroalkanes.

WO 2009/010472 discloses a process for the preparation of halogen containing alkenes over metal fluoride catalysts. Hydrochlorofluoroalkanes are also mentioned as suitable starting materials, but metal fluorides containing chlorine are not mentioned amongst the catalysts.

U.S. Pat. No. 2,673,139 discloses a method for preparing aluminum fluoride catalysts with high activity in dehydrohalogenation reactions. The aluminum fluoride does not contain chlorine.

Mixed chloride fluorides such as barium chloride fluoride are known per se and described in the literature. However, such compounds have not been used as catalysts for dehydrohalogenation reactions before.

The products obtained by dehydrochlorination of hydrochlorofluoroalkanes are interesting intermediates for the synthesis of other hydrofluorocarbons and thus there exists a need for selective dehydrochlorination catalysts and processes.

It was thus an object of the instant invention to provide a process for the dehydrochlorination of hydrochlorofluoroalkanes which yields the dehydrochlorinated products in high yield and with good selectivity.

This object is achieved with the process in accordance with claim 1. Preferred embodiments of the invention are set forth in the dependent claims and the detailed description hereinafter.

Thus, the instant invention relates to a process for the selective dehydrofluorination of hydrochlorofluoroalkanes, said hydrochlorofluoroalkanes comprising at least one chlorine atom and at least one fluorine atom and at least one hydrogen atom at the carbon atom or atoms vicinal to the carbon atom or carbon atoms carrying the chlorine and fluorine atoms.

The hydrochlorofluoroalkanes are not subject to further restrictions as far as their structure is concerned, i.e. any representative of this class of products fulfilling the foregoing prerequisites are suitable for use in the process in accordance with the instant invention.

Generally, the chlorine and fluorine substituents may be located at the same or different carbon atoms in the molecule. If a chlorine and a fluorine substituent are present at different carbon atoms, the hydrogen atoms at carbon atoms vicinal thereto might be attached to different carbon atoms or to the same carbon atom in case at least one chlorine and fluorine substituent are attached to different carbon atoms separated by one carbon atom carrying such hydrogen substituent. In this case, one hydrogen substituent in the molecule is sufficient.

Dehydrohalogenation reactions require this structural feature as in the reaction a hydrogen halide is split off, the hydrogen and the halogen arising from vicinal or neighboured carbon atoms.

Preferred hydrochlorofluoroalkanes which are suitable as educts for the process in accordance with the instant invention comprise either at least one structural element Ia and at least one structural element Ib or at least one structural element II

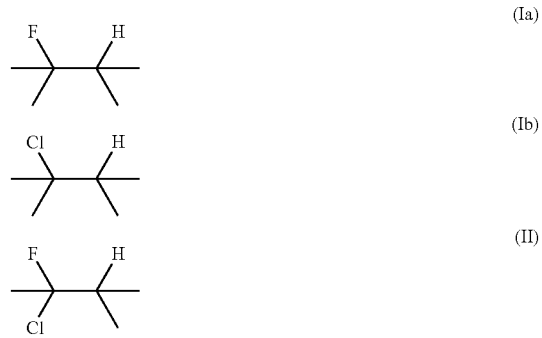

The substituents not shown in the formulae above are preferably selected from $C_1$-$C_8$-alkyl groups, which may be substituted by halogen, in particular by chlorine or fluorine.

A particularly preferred group of hydrochlorofluoroalkanes has the formula III

wherein $R^1$ to $R^4$ are the same or different and independently of each other represent a hydrogen atom, a fluorine atom a $C_1$-$C_8$-alkyl, a $C_1$-$C_8$-fluoroalkyl or a $C_1$-$C_8$-hydrofluoroalkyl group.

Hydrochlorofluoroalkanes having 1 to 6 carbon atoms and preferably 1 to 4 carbon atoms are preferred substrates. 3-chloro-1,1,1,3-tetrafluorobutane is a particularly preferred substrate.

The starting materials which can be used in the process according to the instant invention are known to the skilled man and are available from various sources. 3-chloro-1,1,3,3-tetrafluorobutane (also referred to as HCFC-364mfb according to the generally used nomenclature system used for halogenated hydrocarbons), for example, is inter alia disclosed in U.S. Pat. No. 7,074,434 and other suitable starting materials are described elsewhere.

Various routes for the manufacture of halogenated hydrocarbons with at least 3 carbon atoms are disclosed in WO 2008/043720 to which reference is made herewith for further details.

In the process in accordance with the instant invention hydrochlorofluoroalkanes as described hereinbefore are subjected to a reaction at a temperature preferably above 50° C. with an effective amount of a metal compound having the formula $$(M1)_x(M2)_{1-x}Cl_{1+y}F_{1-y}$$

wherein
M1 and M2 are selected from the group consisting of Ca, Sr and Ba
x is in the range of from 0.2 to 1.0 and
y is in the range of from −0.8 to 0.8.

According to a preferred embodiment of the process in accordance with the instant invention y has a value in the range of from −0.6 to 0.6, more preferably in the range of from −0.6 to 0.3 and even more preferred in the range of from −0.6 to 0. Most preferred y has a value in the range of from −0.4 to 0.

x has preferably a value of at least 0.5, preferably 0.5 to 1.0 and more preferably at least 0.8. Most preferred x is 1, i.e. compounds having only one metal are most preferred.

Among the metals, Ba and Sr are preferred, Ba being the most preferred metal.

Surprisingly it has been found that these catalytically effective metal compounds in this reaction yield the dehydrochlorinated products with a very good selectivity, which is typically at least 80, preferably at least 90%, the remainder being dehydrofluorination products.

Depending on the starting materials more than one dehydrochlorination product and/or more than one dehydrofluorination product as by-product may be obtained and in this case the selectivity is expressed based on the aggregate amount of dehydrochlorination respectively dehydrofluorination products.

Particularly preferably, the selectivity towards dehydrochlorinated products vs. dehydrofluorinated products is at least 92%, most preferred above 94% and may be 100%, i.e. no detectable dehydrofluorination product in particular cases.

In accordance with a preferred embodiment of the instant invention, the metal compound is obtainable by
a) providing a precursor, optionally on a support, wherein the precursor comprises a structure having the formula $(M1)_x(M2)_{1-x}F_{2-\delta-d}B_dL_e$ and
b) reacting the precursor with a hydrochlorofluoroalkane wherein B is a co-ordinatively bound group; L is an organic solvent; x has a value in the range of from 0.2 to 1.0, d is any integer in the range of from 0 to 2, e has a value in the range of from 0 to 1 and 6 has a value in the range of from 0 to 0.1, provided that the denominators representing the number of chlorine and fluorine atoms are positive.

B is preferably an alkoxide, enolate or carboxylic acid group, more preferably an alkoxide group of the formula —O—$C_cH_{2c+1}$ wherein c is any integer from 1 to 6, preferably of from 1 to 3; L is a solvent, preferably an anhydrous organic solvent selected from the group comprising alcohols, ethers, ketones, alkanes and aromatics; and d and e are preferably less than or equal to 1.

Preferred processes for the synthesis of the metal compounds used in accordance with the process of the invention comprising these steps are disclosed in WO 2004/060806 and EP 1,666,411 which are incorporated herein by reference. Such processes are referred to hereinafter as fluorolytic sol-gel synthesis.

The process of the instant invention is not limited, however, to metal compounds obtained in accordance with these references only; any metal compound having the formula according to claim 1 is principally suitable.

According to WO 2004/060806, the precursor is preferably obtained by reacting $(M1)_x(M2)_{1-x}B_2$, wherein B is preferably an alkoxide. B is more preferably dissolved or suspended in an organic solvent L, with of from 2 to 4 equivalents, preferably about 3 equivalents (preferably anhydrous) HF. The HF is preferably dissolved in an organic solvent L', whereby L' can be any of the solvents L and also L' can be equal to or different from L; followed by removing excessive solvents under vacuum at temperatures equal to or less than 350° C., preferably equal to or less than 200° C., still more preferably equal to or less than 100° C. The product obtained thereby is a precursor as defined above.

The preparation of the precursor is preferably performed in a water free solvent, preferably selected from the group consisting of alcohols, ethers, ketones, alkanes, petroleum ether, formic acid, acetic acid or propionic acid. Alcohols of formula $C_cH_{2c+1}OH$ with c=1 to 6, especially 1 to 3, are preferred.

The precursor obtained thereby, in a second step, is further activated by reaction with a (hydro)chlorofluoroalkane, preferably $CCl_2F_2$ or $CHClF_2$ or 3-chloro-1,1,1,3-tetrafluorobutane or the hydrochlorofluoroalkane which is the substrate for the dehydrochlorination reaction.

The suitable metal compounds used in the process in accordance with the instant invention can be prepared as described above by selecting the appropriate precursors.

Metal compounds as obtained by the processes in accordance with WO 2004/060806 and EP 1,666,411 and as described in preferred embodiments hereinbefore have generally a high surface area, preferably in the range of from 40 to 200 $m^2/g$, as measured according to the BET method using $N_2$ (see [0091] of US 2006/052649 A1 for details). Particularly preferred the surface area of the metal compounds thus obtained is in the range of from 50 to 160 $m^2/g$.

The metal compounds can be used as such or on a support material.

Preferably, a support is selected which has a suitably shaped form, is chemically and thermally stable under the conditions of catalyst synthesis and under reaction conditions of catalyst use, mechanically stable, not deteriorating the performance of the catalyst, not interfering with the catalyzed reaction, and enabling anchoring of the metal compound. Any support which meets these requirements can be used. For example, oxides of aluminum or of transition metals are very suitable. Usually, these are present in crystalline form. Activated carbon can also be applied; in a preferred embodiment, aluminum oxide and in an even more preferred embodiment γ-$Al_2O_3$ is used as support.

Preferably, the total amount of metal compound $(M1)_x(M2)_{1-x}Cl_{1+y}F_{1-y}$, especially of $BaCl_{1+y}F_{1-y}$, in the supported catalyst is equal to or greater than 3% by weight, more preferably equal to or more than 4% by weight. Preferably, the content of metal compound in the supported catalyst is equal to or less than 30% by weight, more preferably equal to or less than 20% by weight. In some applications, the content can be equal to or less than 10% by weight. A range with good results is between 4 and 20% by weight. A range of 4 to 8% by weight also gives good results.

The procedure for coating the active metal compound on the catalyst support can be performed by methods known to the skilled man and described in the literature. Two specific alternatives are preferred. Both alternatives comprise a step wherein a support coated with the precursor is formed and a step wherein the activation takes place.

According to the first preferred alternative, the support is impregnated with the precursor compound $(M1)_x(M2)_{1-x}B_d$ as described above. After impregnation, the sol-gel reaction with HF, preferably in a solvent, is performed to obtain the precursor.

In detail, the support, preferably thermally pretreated γ-$Al_2O_3$, is given, preferably under stirring, to a solution of a suitable metal compound, preferably an alkoxide, more preferably an isopropoxide or a methoxide, in an anhydrous organic solvent, preferably an alcohol.

Contact between support and metal compound, preferably under stirring, is continued for a sufficient time to achieve the desired degree of impregnation. For example, after addition of the metal compound, the contact can be continued for equal to or more than 10 minutes, preferably, for equal to or more than 20 minutes. The contact can be extended, if desired, to a very long time, for example, more than 6 hours. It is assumed that the longer the contact, the deeper the metal compound will penetrate into the support. Preferably, the contact between support and metal compound is equal to or less than 6 hours, still more preferably, equal to or less than 2 hours. Often, 20 minutes to 45 minutes are very suitable.

Thereafter, the product obtained after impregnation is transformed into the precursor. A solution of anhydrous hydrogen fluoride in an organic solvent, preferably in a $C_1$ to $C_3$ alcohol or in diethyl ether, is added, preferably under continued stirring, to the system of support and metal compound. The amount of HF is selected so that the molar ratio of HF:metal is preferably equal to or greater than 2. Preferably, it is equal to or lower than 4. Very preferably, the molar ratio of HF:metal is 3±0, 1.

Preferably, the total amount of metal compound starting material in the system is adjusted to correspond to a metal compound content of the final catalyst of equal to or greater than 3% by weight, more preferably equal to or more than 4% by weight. Preferably, the content of metal compound in the supported catalyst is equal to or less than 30% by weight, more preferably equal to or less than 20% by weight, sometimes even equal to or less than 10% by weight, based on the weight of the catalyst. However, it is possible to use the metal compound as such also as support, i.e. in this case the content of metal compound may be up to 100% by weight of the catalyst. Often, the amount is adjusted so that the content of the metal compound in the supported catalyst is preferably between 4 and 20% by weight. Often, a supported catalyst with 4 to 8% by weight metal compound is produced.

According to the second preferred alternative, the organic metal compound, preferably the barium compound, preferably in the form of a solution, is first reacted in the sol-gel type reaction with the appropriate amount of HF solution, preferably under stirring, followed by addition of the respective support, whereby the materials used and their relative amounts are as described above, especially in view of the alternative a).

After the reaction of the metal compound and HF to form the precursor has taken place, be it after impregnation of the carrier according to the first alternative, or before contact with the carrier according to the second alternative, excessive solvent(s) is or are removed. Preferably, this is performed in a gentle manner, preferably under vacuum. The removal advantageously is supported by warming or heating. Preferably, the temperature is equal to or higher than 25° C., more preferably, it is equal to or higher than 30° C. Preferably, the temperature is equal to or lower than 200° C., more preferably, it is equal to or lower than 150° C. A preferred range is 40 to 90° C. Both procedures a) or b) and subsequent solvent removal provide a supported precursor.

The precursor already has catalytic activity. The catalytic activity can be greatly enhanced if the precursor is activated by subsequent reaction with a gaseous hydrochlorofluoroalkane at elevated temperature.

They can be applied in admixture with up to 95% (v/v), of an inert gas such as nitrogen or a noble gas, preferably argon; the content of the inert gas is preferably equal to or higher than 75% (v/v); it is preferably equal to or lower than to 90% (v/v). Especially preferably, the inert gas content is 85±5% (v/v). The temperature in step A1) preferably is equal to or higher than 150° C., more preferably, equal to or higher than 180° C. Preferably, the temperature is equal to or lower than 400° C.

Whereas any hydrochlorofluoroalkane is principally suitable for the activation step, it has proven advantageous in a number of cases to carry out the activation with the same hydrochlorofluoroalkane which is the substrate for the dehydrochlorination reaction. By doing so, the activation can be carried out in-situ, i.e. immediately prior to the dehydrochlorination reaction in the same reactor.

The activation can be monitored by elementary analysis of the reaction mixture at various times. The chlorine content of the metal compound increases up to a certain value at which it remains. Once the chlorine content remains constant, the activation is completed. It can be assumed that the fluoride precursor is chlorinated by virtue of HCl produced in the dehydrochlorination of the hydrochlorofluoroalkane.

In a subsequent step, flushing is optionally performed to remove volatiles from the catalyst. It is preferred to perform a flushing step. Flushing can be stopped when the desired degree of purification has been achieved. It can be performed for an extended time, for example, up to ten hours or more. Preferably, flushing is performed for equal to or less than 6 hours. Preferably, it is performed for equal to or more than 1 hour. The temperature during flushing is preferably equal to or higher than 200° C. Preferably, it is equal to or lower than 300° C. A temperature range of from 240° C. and 260° C. is very suitable.

The supported catalyst can be prepared in the form of a powder, in the form of pellets, beads, extrudates and other formed bodies. Beads with a diameter in the range of, for example, 1 to 10 mm are very suitable for the dehydrochlorination process according to the instant invention.

The dehydrochlorination reaction in the process of the present invention takes place very selectively and in high yields. The temperature at which dehydrochlorination occurs depends on the respective starting compound. Generally, the reaction temperature is equal to or higher than 50° C., preferably equal to or higher than 120° C. The reaction can be performed at even lower temperature, but in some cases, the speed of reaction may be considered to be too low. Generally, the reaction is performed at a temperature equal to or lower than 300° C., preferably equal to or lower than 250° C., and very preferably equal to or lower than 230° C. The catalyst is very active for extended periods of time when the reaction temperature is equal to or lower than 400° C. The result of the dehydrochlorination is very good at temperatures e.g. above 100° C. The long-term performance of the catalyst is especially good if it is operated at temperatures equal to or below 400° C.

The reaction temperature is preferably equal to or higher than 120° C. The speed of reaction can be accelerated if the reaction temperature is equal to or higher than 150° C. Often, performing the reaction in a range of from 180° C. to 250° C. allows a high reaction speed with high conversion. A fast reaction and high conversion are observed even if the dehydrochlorination temperature is equal to or higher than 250° C.

Generally, the selectivity of the dehydrochlorination decreases slightly with increasing temperature, i.e. at higher reaction temperatures dehydrofluorination is increasingly observed. The skilled man will select the reaction conditions so as to obtain the best conditions for the desired conversion and selectivity.

Depending on the structure of the starting material in the dehydrochlorination isomers may be formed, which can then be separated by distillation, if required. In the dehydrochlorination of HCFC-364 having the formula $CH_3-CFCl-CH_2-CF_3$, for example, three isomers are formed namely 1,1,1,3-tetrafluorobut-3-ene and the E- and Z-isomers of 1,1,1,3-tetrafluoro-but-2-ene. With other starting materials the respective isomers can be obtained.

In some cases, the balance between high reaction speed and high selectivity may favour operation at relatively low reaction temperature.

If one observes diminishing catalyst activity, e.g. after long reaction periods, or if the reaction temperature was selected too high, a regeneration of the catalyst is possible. Oxidizing gases can be passed at elevated temperatures through the reactor, e.g. air or oxygen. As is described below, the catalytic activity can be extended by passing a hydrochlorofluoroalkane/nitrogen (or inert gas) mixture through the reactor.

The reaction can be performed batch wise or continuously. It is preferred to operate in the gas phase, especially continuously.

If desired, the halogenated hydrocarbon used as starting material can be diluted before the dehydrochlorination reaction with an inert gas, for example, nitrogen, or a noble gas, for example, argon. In this case, the halogenated hydrocarbon preferably is present in the gas mixture with inert gas in an amount of equal to or more than 10 vol. %. Preferably, it is present in an amount of equal to or less than 75 vol. %, more preferably in an amount of equal to or less than 50 vol. %, and especially preferably equal to or less than 35 vol. %. The productivity of the catalyst was in some cases observed to be higher when using inert gas (nitrogen for example).

Accordingly, mixtures comprising or consisting of nitrogen and a hydrochlorofluoroalkane with 2 to 5 carbon atoms in a molar ratio of $N_2$:hydrochlorofluoroalkane of (2-9):1, preferably of (3-6):1 can be passed over the catalyst as described above. Mixtures comprising or consisting of nitrogen and a hydrochlorofluoroalkane with 2 to 5 carbon atoms in a molar ratio of $N_2$:hydrochlorofluoroalkane of (3-5):1 are especially preferred. Especially preferred are mixtures comprising or consisting of $N_2$ and a $C_3$ or $C_4$ hydrochlorofluoroalkane in a molar ratio of (2-9):1, preferably (3-6):1, more preferably (3-5):1.

The process in accordance with the instant invention yields the desired products with good yield and with a good conversion. The products of the dehydrochlorination can be used for various applications. Chlorine-free endproducts obtained by dehydrochlorination of hydrochlorofluoroalkanes with one chlorine atom are useful as such or after saturation of the double bond as so called second-generation halogenated hydrocarbons.

Another aspect of the present invention is the use of a metal compound of formula $$(M1)_x(M2)_{1-x}Cl_{1+y}F_{1-y}$$

wherein
M1 is selected from the group consisting of Ca, Sr and Ba
x is in the range of from 0.2 to 1.0 and
y is in the range of from −0.8 to 0.8.
as a catalyst for the selective dehydrochlorination of hydrochlorofluoroalkanes. Preferred metal compounds, starting compounds, reaction products and reaction conditions are those given above.

Should the disclosure of any patents, patent applications, and publications which are incorporated herein by reference conflict with the description of the present application to the extent that it may render a term unclear, the present description shall take precedence.

EXAMPLES

Catalytically active Barium compounds were prepared in accordance with the so-called water-free fluorolytic Sol-Gel method in accordance with Kemnitz, E. et al., "Amorphe Metallfluoride mit aussergewöhnlich grosser spezifischer Oberfläche", Angew. Chem. 2003, 115(35) and Rüdiger, S. and Kemnitz, E., "The fluorolytic sol-gel method to metal fluorides—a versatile process opening up a variety of application fields, Dalton Trans. 2008, pp. 1117-1127.

In the first step a respective Ba precursor compound was reacted with HF in methanol. Thereby sol- or gel-like network structures were obtained. Thereafter the volatile substances were removed by drying at 100° C. under vacuum for two hours.

The resulting Xerogel (BaF2) was then subjected to a gas-phase activation with 3-chloro-1,1,1,3-tetrafluorobutane (S-364) at a temperature of 200° C.

The carbon content of the BaF2 was very low, indicating that the organic components formed during its synthesis had been substantially completely removed during the subsequent drying process.

The chlorine content of the product increased initially rapidly from 0 to 10.4 wt. % within two hours, reaching a constant value of 13.4 wt. % after 20 hours. A chlorine content of 13.4 wt. % corresponds to a stoichiometric formula 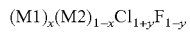, i.e. y in this experiment had a value of −0.3 and x was 1.

The catalytic dehydrochlorination of 3-chloro-1,1,1,3-tetrafluorobutane (S-364) was carried out as follows:

A heatable quartz reactor having an internal diameter of 8 mm and an external diameter of 10 mm was filled with 200 mg of the respective catalytically active compound which was fixed in the middle of the reactor by quartz wool plugs. A gas stream of 25 ml/min of a mixture of 3-chloro-1,1,1,3-tetrafluorobutane and nitrogen (volume ratio 1:4) was introduced into the reactor which was kept at a temperature of 150, 200 or 230° C. After passage through the reactor, the gas stream was carried through a 0.5 molar solution of sodium hydrogen carbonate to neutralize the gaseous acids produced during the reaction (HCl, $SiF_4$). Thereafter samples were taken which were analyzed directly by gas chromatography and GC-MS respectively (in this case the gas stream was condensed in trichloromethane for injection into the GC-MS system).

Conversion at 200 and 230° C. was approximately 95% whereas at 150° C. conversion dropped to 20-40%.

Table 1 shows the results of the dehydrochlorination at the respective temperatures and the relative selectivity towards the three possible products Z- and E-1,1,1,3-tetrafluorobut-2-ene (TFBE1 and TFBE2 respectively) and 1,1,1,3-tetrafluorobut-3-ene (TFBE3). Selectivity for dehydrochlorination denotes the percentage of dehydrochlorinated products in the reaction mixture, the remainder being dehydrofluorinated products.

TABLE 1

| Temperature ° C. | Selectivity TFBE1 | Selectivity TFBE1 | Selectivity TFBE1 | Selectivity dehydrochlorination |
|---|---|---|---|---|
| 150 | 0.24 | 0.13 | 0.57 | 0.94 |
| 200 | 0.12 | 0.10 | 0.73 | 0.95 |
| 230 | 0.10 | 0.09 | 0.69 | 0.88 |

The results show that selectivity slightly decreased with increasing temperature. Due to the significantly lower conversion at 150° C. as indicated above, the margin of error of the values at this temperature is higher than at 200 and 230° C. as there is a significant amount of starting material in the reaction mixture.

In a second row of experiments at 200° C., the flow rate of the gas stream comprising 3-chloro-1,1,1,3-tetrafluorobutane and nitrogen was increased to 50 ml/min, thereby reducing the contact time from 0.5 s to 0.25 s. The conversion dropped to 70-75% whereas the selectivity towards dehydrochlorination was not affected significantly.

Further embodiments of the instant invention by modifying the reaction conditions or the compositions of the catalytically active metal compound are evident to the skilled man.

The invention claimed is:

1. A process for the catalytic dehydrochlorination of a hydrochlorofluoroalkane, said hydrochlorofluoroalkane comprising a carbon atom or carbon atoms carrying at least one chlorine atom and at least one fluorine atom, and further comprising at least one hydrogen atom on a carbon atom vicinal to the carbon atom or to the carbon atoms carrying the at least one chlorine and at least one fluorine atom, said process comprising subjecting the hydrochlorofluoroalkane to a dehydrochlorination reaction by contacting the hydrochlorofluoroalkane with a catalytically active metal compound of formula

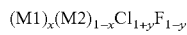

wherein
M1 and M2 are selected from the group consisting of Ca, Sr, and Ba;
x is in the range of from 0.2 to 1.0; and
y is in the range of from −0.8 to 0.8.

2. The process in accordance with claim 1, wherein y is in the range of from −0.6. to 0.6.

3. The process in accordance with claim 2, wherein y is in the range of from −0.6 to 0.

4. The process in accordance with claim 1, wherein x is at least 0.5.

5. The process in accordance with claim 4, wherein x is at least 0.8.

6. The process in accordance with claim 5, wherein x is 1.

7. The process in accordance with claim 1, wherein M1 is Ba.

8. The process in accordance with claim 1, wherein the catalytically active metal compound is obtained by
a) providing a precursor, optionally on a support, wherein the precursor comprises a structure having the formula $(M1)_x(M2)_{1-x}F_{2-\delta-d}B_dL_e$,
wherein B is a co-ordinately bound group; wherein L is an organic solvent; wherein x is in the range of from 0.2 to 1.0; wherein d is any integer in the range of from 0 to 3; wherein e has a value in the range of from 0 to 1; and wherein δ has a value in the range of from 0 to 0.1, provided that the denominators representing the number of chlorine and fluorine atoms are positive; and
b) activating the precursor with a hydrochlorofluoroalkane, thereby generating the catalytically active metal compound.

9. A method for the selective dehydrochlorination of a hydrochlorofluoroalkane, said method comprising: using, as a catalyst, a metal compound of formula

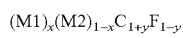

wherein
M1 and M2 are selected from the group consisting of Ca, Sr, and Ba;
x is in the range of from 0.2 to 1.0; and
y is in the range of from −0.8 to 0.8.

10. The process in accordance with claim 1, wherein the hydrochlorofluoroalkane comprises at least one structural element Ia and at least one structural element Ib or at least one structural element II

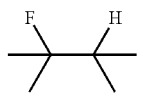

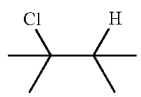

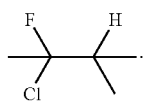

11. The process in accordance with claim 1, wherein said hydrochlorofluoroalkane has a formula III

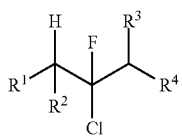

wherein $R^1$ to $R^4$ are the same or different and, independently of each other, represent a hydrogen atom, a fluorine atom, a $C_1$-$C_8$-alkyl, a $C_1$-$C_8$-fluoroalkyl, or $C_1$-$C_8$-hydrofluoroalkyl group.

12. The process in accordance with claim 1, wherein said catalytically active metal compound has a surface according to the BET method using $N_2$ of from 40 to 200 m²/g.

13. The process in accordance with claim 1, wherein said catalytically active metal compound has a surface according to the BET method using $N_2$ of from 50 to 160 m²/g.

14. The process in accordance with claim 1, wherein said hydrochlorofluoroalkane is subjected to the dehydrochlorination reaction in the presence of said catalytically active metal compound at a reaction temperature equal to or lower than 400° C.

15. The process in accordance with claim 14, wherein the reaction temperature is equal to or lower than 300° C.

16. The process in accordance with claim 15, wherein the reaction temperature is equal to or lower than 250° C.

17. The process in accordance with claim 16, wherein the reaction temperature is equal to or lower than 230° C.

18. The process in accordance with claim 1, wherein said catalytically active metal compound is regenerated in a reactor wherein oxidizing gases are passed through the reactor.

19. The process in accordance with claim 1, wherein said hydrochlorofluoroalkane is diluted with an inert gas before the dehydrochlorination reaction.

20. The process in accordance with claim 1, wherein 3-chloro-1,1,1,3-fluorobutane is applied as starting material for said hydrochlorofluoroalkane.

* * * * *